United States Patent [19]

Gallo

[11] 3,967,578

[45] July 6, 1976

[54] MOISTURE GAUGE FOR A HANGING POTTED PLANT

[76] Inventor: Joseph Sebato Gallo, 58 Peach St., Walpole, Mass. 02081

[22] Filed: May 12, 1975

[21] Appl. No.: 576,885

[52] U.S. Cl. .............................. 116/114 R; 47/35; 73/73; 116/DIG. 32; 177/50; 177/225
[51] Int. Cl.² .................... G01G 3/08; G01D 18/00; G01N 5/00
[58] Field of Search .............................. 73/73, 171; 116/DIG. 32, 69, 114 R, 114 S; 177/225, 229, 234, 50, 45; 239/65, 71; 47/35

[56] References Cited
UNITED STATES PATENTS

| | | | |
|---|---|---|---|
| 1,190,632 | 7/1916 | Collette | 177/45 X |
| 3,818,633 | 6/1974 | Sable | 47/35 X |

Primary Examiner—Richard C. Queisser
Assistant Examiner—Daniel M. Yasich
Attorney, Agent, or Firm—Maxwell Fish

[57] ABSTRACT

A moisture gauge for a hanging potted plant, which comprises a generally U-shaped spring element comprising a spring coil and a pair of approximately parallel arms extending from said spring coil shaped to provide notches opposite one-another at spaced intervals along the facing edges of the two arms, one of said arms terminating in an indicator, the other arm having a cross-wise extension providing a moisture indicating scale. Adjoining segments of the pendant support by which the hanging potted plant is supported are connected respectively to oppositely notched portions of the two arms selected with reference to the weight of the potted plant when fully watered, so that the indicator will be extended as accurately as possible to the fully watered position.

4 Claims, 2 Drawing Figures

U.S. Patent  July 6, 1976  3,967,578
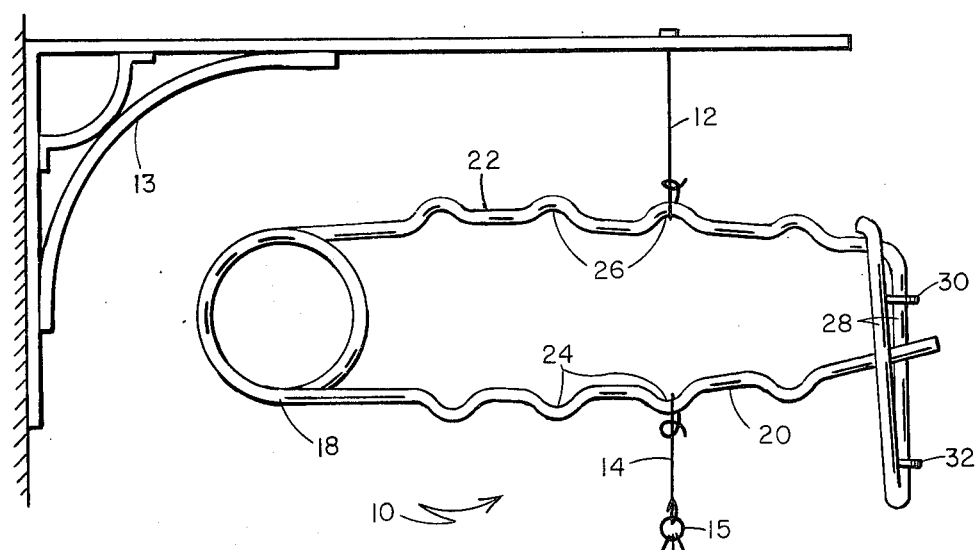
FIG. 1
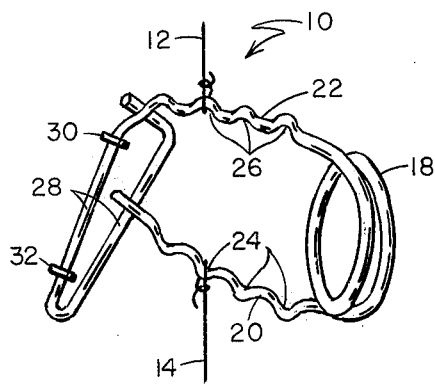
FIG. 2

MOISTURE GAUGE FOR A HANGING POTTED PLANT

BACKGROUND OF THE INVENTION

FIELD OF THE INVENTION

The present invention relates to a moisture gauge suitable for indicating the moisture content of a hanging potted plant.

SUMMARY OF THE INVENTION

It is a principal object of the invention to provide a moisture gauge which can be inserted between two adjacent segments of the pendant support of a hanging potted plant to provide a visible check on the amount of moisture contained therein.

It is a further object of the invention to provide a simple, inexpensive gauge which may be constructed from a single length of spring wire, to provide an accurate indication of the moisture content of the potted plant.

It is another object of the invention to provide a moisture gauge of this general description which is readily adjustable to indicate accurately the maximum and minimum moisture contents of hanging potted plants for a wide range of sizes and weights of such plants.

Other objects and advantageous features of the invention will be apparent from the description and claims.

BRIEF DESCRIPTION OF THE DRAWING

The nature and characteristic features of the invention will be more readily understood from the following description taken in connection with the accompanying drawing forming part thereof, in which FIG. 1 is a view in side elevation of the moisture gauge suspended between two segments of a pendant support for a hanging potted plant attached to a wall bracket; and FIG. 2 is a perspective view of the moisture gauge shown in FIG. 1 with the adjacent segments of the pendant support attached to opposed notches.

It should, of course, be understood that the description and drawing herein are illustrative merely, and that various modifications and changes can be made in the structure disclosed without departing from the spirit of the invention.

Like numerals refer to like parts throughout the several views.

DESCRIPTION OF THE PREFERRED EMBODIMENT

The moisture gauge which forms the subject matter of the invention consists of a generally U-shaped spring element 10 adapted to be connected, as shown in FIG. 1, between adjacent segments 12 and 14 of a pendant support for a hanging plant 16. More specifically, the gauge 10 consists of a spring coil 18 and two arms 20 and 22 which extend away therefrom in substantially parallel relation. A series of short bends or waves in each of the arms provide notches 24 and 26 spaced along the inner edges of the respective arms. The notches 24 and 26 are disposed opposite one another in pairs which provide alternative stations along the length of the two arms for attachment of the segments 12 and 14. When the segments 12 and 14 of the pendant support are connected respectively to a particular pair of opposed notches 24 and 26, and the weight of the potted plant 18 is brought to bear on the pendant support, the segment 14 will line up directly beneath the segment 12, causing the moisture gauge 10 to assume a longitudinally horizontal position in which the arm 20 is disposed directly beneath, and tends to be pulled away from the arm 22 by the weight of the potted plant 16. Since the weight of the potted plant will vary substantially in proportion to any gain or loss of moisture contained therein, the position of the arm 20 with relation to the arm 22 secured to the upper segment 12 of the pendant support may be taken as an indication of the moisture content of the potted plant.

The upper arm 22 of the plant moisture gauge is formed at its outer end with a cross-wise extension 28 disposed at right angles to the arm 22, and extending downwardly across the end of the indicator arm 20. At its lower end the extension is doubled over to form a slot, within which the indicator arm is guided between high and low plant moisture content positions. Two rubber washers designated as markers 30 and 32 located adjacent the upper and lower ends of the slot formed by the doubled-over portion of the extension 28 indicate respectively the upper and lower limits of movement permitted to the indicator arm 20.

The number of pairs of pairs of notches 24,26 spaced along the length of the two arms 20,22 of the moisture gauge represent a means of adjusting the gauge for measuring the level of moisture content in potted plants of different sizes and weights. The illustrated gauge, for example, may be adjusted to measure maximum and minimum levels of moisture in potted plants ranging from 3 pounds to 25 pounds.

It has been assumed that the weight of the potted plant, when dry and in need of watering, will be just sufficient to hold the indicator arm 20 opposite the marker 30, and when fully watered, will be just sufficient to move the indicator arm 20 to a position opposite the marker 32. If, however, a heavier potted plant is assumed, the segments 12 and 14 of the pendant support must be moved to a pair of notches 24,26 closer to the spring coil 18 in order to correspondingly restrict the downward movement of the indicator arm 20 to the limit position indicated by the marker 32. A potted plant substantially lighter than the potted plant illustrated in the drawing, on the other hand, will move the indicator arm 20 properly between the dry position indicated by the marker 30 and the fully watered position indicated by the marker 32 only after the segments 12 and 14 of the pendant support are attached to a pair of notches 24,26 nearer the outer ends of arms 20,22, thereby increasing the downward pull exerted upon the arm 20 which would not otherwise move to the fully watered position indicated by the marker 32.

The invention having been described, what is claimed is:

1. A moisture weight gauge for insertion between two adjacent segments, of a pendant support for a hanging potted plant, having, in combination,
    a generally U-shaped spring wire support element including a spring coil,
    two arms extending from said spring coil in approximately parallel relation,
    one of said arms terminating in a pointer,
    the other of said arms having a calibrated extension cross-wise of said arms providing a guideway for directing relative movement of the guideway and said pointer arm toward and away from one another, and means for maintaining substantially constant limits of movement of said pointer arm relative to said guideway compensating for differences in plant weight which comprises a plurality of means for selective attachment of said segments at spaced points or intervals along the length of each arm, said means of attachment being paired, one of a pair on each arm, and equally distant from said spring coil.

2. A moisture weight gauge according to claim 1, in which said points of attachment comprise a series of bends in each arm providing a series of opposed notches facing one another along the inner faces of the two arms.

3. A moisture weight gauge according to claim 2, in which the cross-wise extension is doubled-over to form the guideway for the indicator arm constraining the arms to move only toward and away from one another.

4. A moisture weight gauge according to claim 3 in which two markers are located on the cross-wise extension to mark alternative extreme positions of the pointer arm relative to the cross-wise extension, and thereby to indicate when the plant is fully watered or dry.

* * * * *